US011160603B2

(12) United States Patent
Shvetsov et al.

(10) Patent No.: US 11,160,603 B2
(45) Date of Patent: Nov. 2, 2021

(54) ELECTROSURGICAL DEVICE WITH VACUUM PORT

(71) Applicant: Buffalo Filter LLC, Lancaster, NY (US)

(72) Inventors: Kyrylo Shvetsov, Depew, NY (US); Gregory Pepe, Lancaster, NY (US); Michael J. Miller, Depew, NY (US); Joseph P. Callahan, Lancaster, NY (US)

(73) Assignee: Buffalo Filter LLC, Lancaster, NY (US)

( * ) Notice: Subject to any disclaimer, the term of this patent is extended or adjusted under 35 U.S.C. 154(b) by 286 days.

(21) Appl. No.: 15/556,580

(22) PCT Filed: Mar. 4, 2016

(86) PCT No.: PCT/US2016/021008
§ 371 (c)(1),
(2) Date: Sep. 7, 2017

(87) PCT Pub. No.: WO2016/144804
PCT Pub. Date: Sep. 15, 2016

(65) Prior Publication Data
US 2018/0036064 A1    Feb. 8, 2018

Related U.S. Application Data

(60) Provisional application No. 62/129,328, filed on Mar. 6, 2015.

(51) Int. Cl.
*A61B 18/12*    (2006.01)
*A61B 18/14*    (2006.01)
(Continued)

(52) U.S. Cl.
CPC .......... *A61B 18/1402* (2013.01); *A61B 90/98* (2016.02); *A61B 90/30* (2016.02);
(Continued)

(58) Field of Classification Search
CPC ..... A61B 18/1402; A61B 90/98; A61B 90/30; A61B 2017/00734; A61B 2017/00876;
(Continued)

(56) References Cited

U.S. PATENT DOCUMENTS 4,655,215 A * 4/1987 Pike ................... A61B 18/1402
606/42
5,174,300 A * 12/1992 Bales ................. A61B 17/2909
600/564

(Continued)

OTHER PUBLICATIONS

ISA/US, International Search Report and Written Opinion from PCT/US2016/021008, dated Jul. 13, 2016.
(Continued)

*Primary Examiner* — Daniel W Fowler
(74) *Attorney, Agent, or Firm* — Timothy W. Menasco, Esq.; Jacob D. Merrill, Esq.; Harter Secrest & Emery LLP (57) ABSTRACT

Embodiments of the present disclosure provide an electrosurgical device. The electrosurgical device includes an electrode having a first portion whose exterior is electrically uninsulated, a second portion whose exterior is electrically insulated, and a third portion. The device includes an elongated hollow body formed by a first member and a second member. The second member is capable of rotating relative to the first member. The hollow body has an internal cavity, a front end, a rear end, an external surface, and an electrical wire arranged within the body. The hollow body is configured to reversibly receive the third portion of the electrode at the front end of the body such that electrical contact is made between the electrode and the electrical wire and the
(Continued)

second portion of the electrode is not surrounded by the hollow body. The device includes a first button, a vacuum tube and a vacuum outlet.

16 Claims, 7 Drawing Sheets

(51) Int. Cl.
*A61B 90/98* (2016.01)
*A61B 18/00* (2006.01)
*A61B 90/30* (2016.01)
*A61B 17/00* (2006.01)

(52) U.S. Cl.
CPC .............. *A61B 2017/00734* (2013.01); *A61B 2017/00876* (2013.01); *A61B 2018/0072* (2013.01); *A61B 2018/00077* (2013.01); *A61B 2018/00172* (2013.01); *A61B 2018/00202* (2013.01); *A61B 2018/00642* (2013.01); *A61B 2018/00702* (2013.01); *A61B 2018/00958* (2013.01); *A61B 2218/007* (2013.01); *A61B 2218/008* (2013.01)

(58) Field of Classification Search
CPC ........... A61B 2018/00077; A61B 2018/00172; A61B 2018/00202; A61B 2018/00642; A61B 2018/00702; A61B 2018/0072; A61B 2018/00958; A61B 2218/007; A61B 2218/008
See application file for complete search history.

(56) References Cited

U.S. PATENT DOCUMENTS

| | | | |
|---|---|---|---|
| 5,451,222 A | 9/1995 | DeMaagd | |
| 8,057,470 B2* | 11/2011 | Lee | A61B 18/1402 606/41 |
| 8,641,488 B1 | 2/2014 | Shvetsov et al. | |
| 2002/0019631 A1* | 2/2002 | Kidder | A61B 18/1402 606/42 |
| 2009/0062791 A1 | 3/2009 | Lee et al. | |
| 2011/0190768 A1* | 8/2011 | Shvetsov | A61B 18/18 606/48 |
| 2014/0257273 A1 | 9/2014 | Cosmescu | |
| 2014/0276763 A1 | 9/2014 | Greep et al. | |
| 2014/0276801 A1* | 9/2014 | Juergens | A61N 1/04 606/42 |

OTHER PUBLICATIONS

Partial Supplementary European Search Report from EP16762247. 1, dated Jan. 3, 2019.

* cited by examiner

ELECTROSURGICAL DEVICE WITH VACUUM PORT

TECHNICAL FIELD

The present invention relates generally to smoke evacuation and, more specifically, to an electrosurgical device with smoke evacuation during medical procedures.

BACKGROUND

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

With parenthetical reference to the corresponding parts portions or surfaces of the disclosed embodiments, merely for the purposes of illustration and not by way of limitation, the present embodiment provides an electrosurgical device having an electrode (11) with a first portion (12) with an exterior that is electrically uninsulated, a second portion (13) with an exterior that is electrically insulated, and a third portion (14). An elongated hollow body (22) is formed by a first member (23) and a second member (24). The second member (24) is capable of rotating relative to the first member (23). The body (22) has an internal cavity (26), a front end (28), a rear end (29), an external surface (17), and an electrical wire (25) arranged within the body (22). The hollow body (22) is configured to reversibly receive the third portion (14) of the electrode (11) at the front end (28) of the body (22) such that electrical contact is made between the electrode (11) and the electrical wire (25). In use, the second portion (13) of the electrode (11) is not surrounded by the hollow body (22). A first button (18) is arranged on the body's external surface for controlling a current flow at a first level. A vacuum tube (16) is slidably engaged by the body (22), and the vacuum tube (16) is arranged adjacent the electrode (11). A vacuum outlet port (30) is arranged near the rear end (29), and the outlet port (30), internal cavity (26), and vacuum inlet (15) are in fluid communication with each other.

The body (22) may be ergonomically shaped to be received by a user's hand. The inlet may be shaped to face away from the electrode (11). The body (22) may be pencil shaped and may contain friction striations. The friction striations may be curved. The electrode may be mono-polar, bipolar, or sesqui-polar.

The device may have a second button (19) for controlling a current flow at a second level to the electrode (11), and may have a third button for smoke evacuator control.

The device may also have: a light source arranged to illuminate an area near the electrode, a battery for providing power to the light source, and a button for controlling the illumination light. The device may also include a swivel joint (39) between the body and the outlet port. The electrical wire (25) may pass through the swivel joint.

A filter may be arranged within the internal cavity, and the filter may have an RFID tag containing filter information. The vacuum inlet (15) may have a substantially rectangular cross section. The vacuum inlet (15) may also have a V-shape to prove easier access to the electrode for removal and replacement. Also, the device may include an oxygen sensor near the vacuum inlet (15) or at other locations in the air flow path to detect the level of oxygen in the air stream. If the oxygen level is too high, the oxygen sensor causes power to the electrode (11) to be shut off.

The device has means for removing the electrode without electrically contacting the electrode. The device also has means for preventing the vacuum tube from obstructing a user's view which may comprise a slidable engagement between the vacuum tube and the body. The means for preventing the vacuum tube from obstructing a user's view may also comprise an inlet shaped to have a cross section perpendicular to a user's line of sight towards the electrode when using the device. The means for removing the electrode without electrically contracting the electrode may comprise an insulation coating on the electrode which remains accessible to a user's hand when the electrode is received by the body.

The means for preventing the vacuum tube from obstructing a user's view may comprise a vacuum tube made of clear material.

In one embodiment, the first member (23) has an end (100) facing the second member (24). The end (100) has an opening (103) with a first diameter (106). The first member (23) has a chamber (109) defined therein. The chamber (109) has a second diameter (112) larger than the first diameter (106). The chamber (109) is bordered by a side wall (115) and a shoulder (118) extends between the side wall (115) and the opening (103). The chamber (109) is bordered by a bottom wall (128) with a first engagement surface (121) disposed thereon. The chamber (109) is disposed in fluid communication with the cavity (26).

The second member (24) has a body (200) having a first end (203) and a second end (206). The body (200) has a first portion (209) having an outside diameter (212) sized to fit inside the opening (103) in the first member (100). The body (200) has a flange (215) at the second end (206). The second member (24) has a second engaging surface (218) disposed near the second end (206) of the body (200). The second engaging surface (218) is configured to engage with the first engagement surface (121) to prevent rotation between the first member (23) and the second member (24) when the flange (215) is acted on by a biasing member (221).

DETAILED DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, the present invention broadly provides an electrosurgical device having a vacuum port, generally indicated at 10, which is particularly adapted for (but is not limited to) suctioning smoke during electrosurgery.

Figure 1:
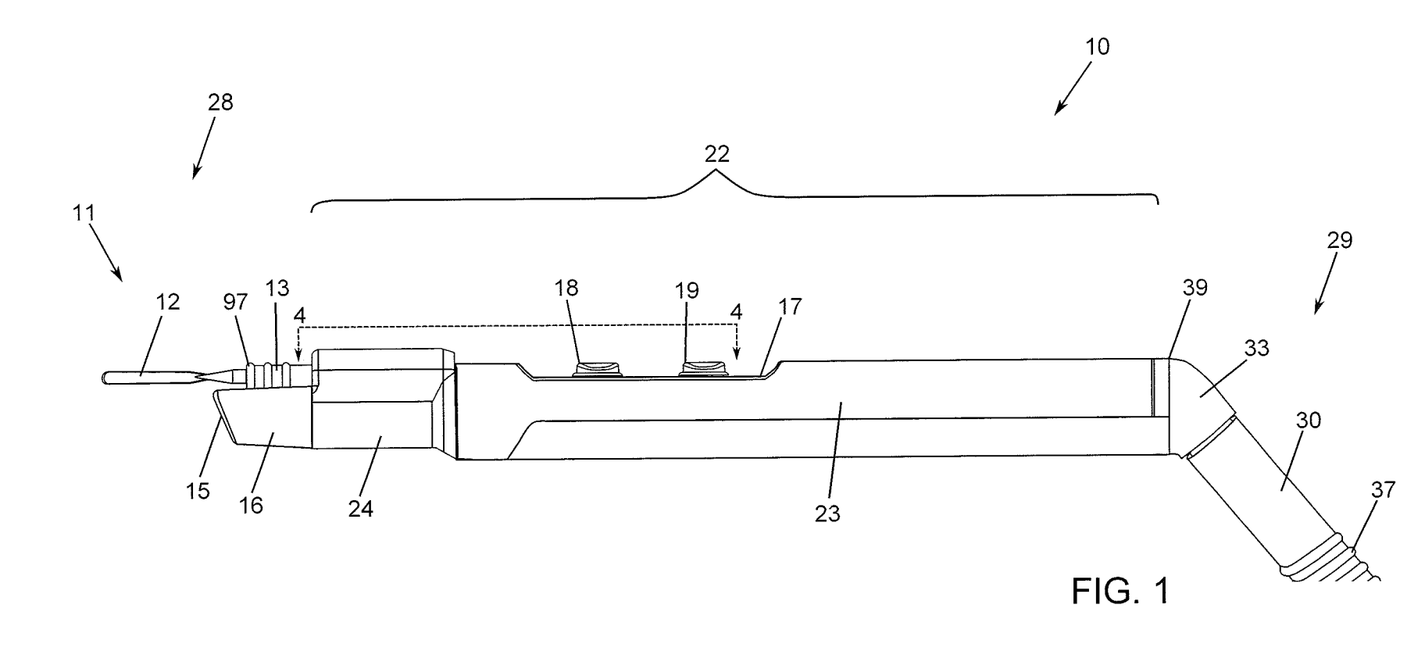
FIG. 1 is a side elevational view showing a first embodiment of the electrosurgical device in a vacuum tube retracted configuration.

In FIG. 1, the electrosurgical device 10 is shown as broadly including hollow body 22 formed by a first member 23 and a second member 24. Second member 24 is capable of rotating from a first position to a second position relative to the first member 23 as described in detail herein. Vacuum tube 16 and electrode 11 are both disposed on second member 24 such that they have a common axis of rotation. The hollow body 22 has a front end 28 for holding electrode 11, a rear end 29 for holding vacuum port 30, an electrical wire 25 (FIGS. 3-4), a coagulate button 18, a cut button 19, and a vacuum tube 16. Vacuum tube 16 is slidably engaged by hollow body 22 and is shown in the retracted configuration in FIG. 1. The device may also include a third button for smoke evacuator control. Also, an oxygen sensor may be disposed near the vacuum inlet 15 or at other locations in the air pathway to cause power to the electrode 11 to be shut off if the oxygen level is too high.

Figure 3:
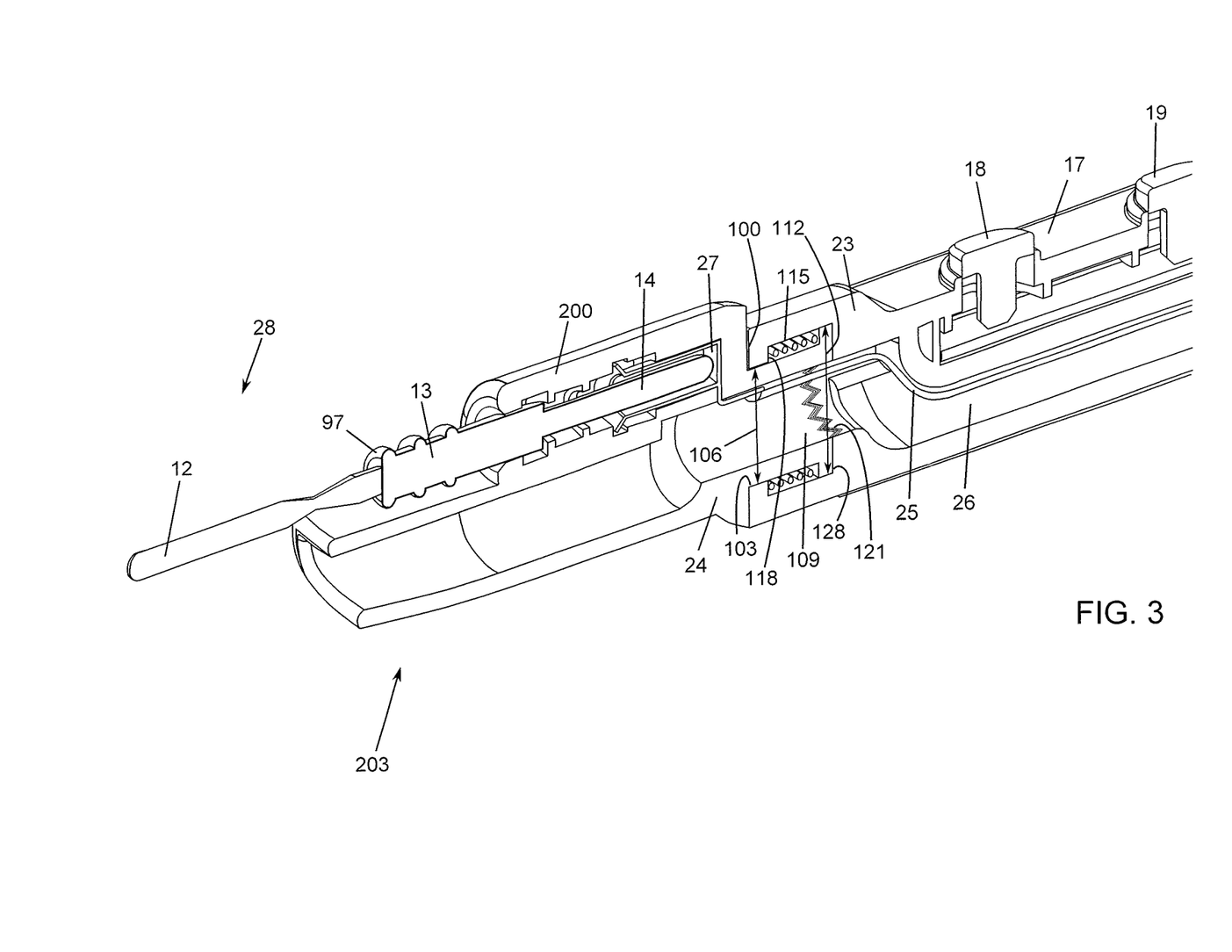
FIG. 3 is a partial sectional side view taken along lines 3-3 of FIG. 2.
Figure 4:
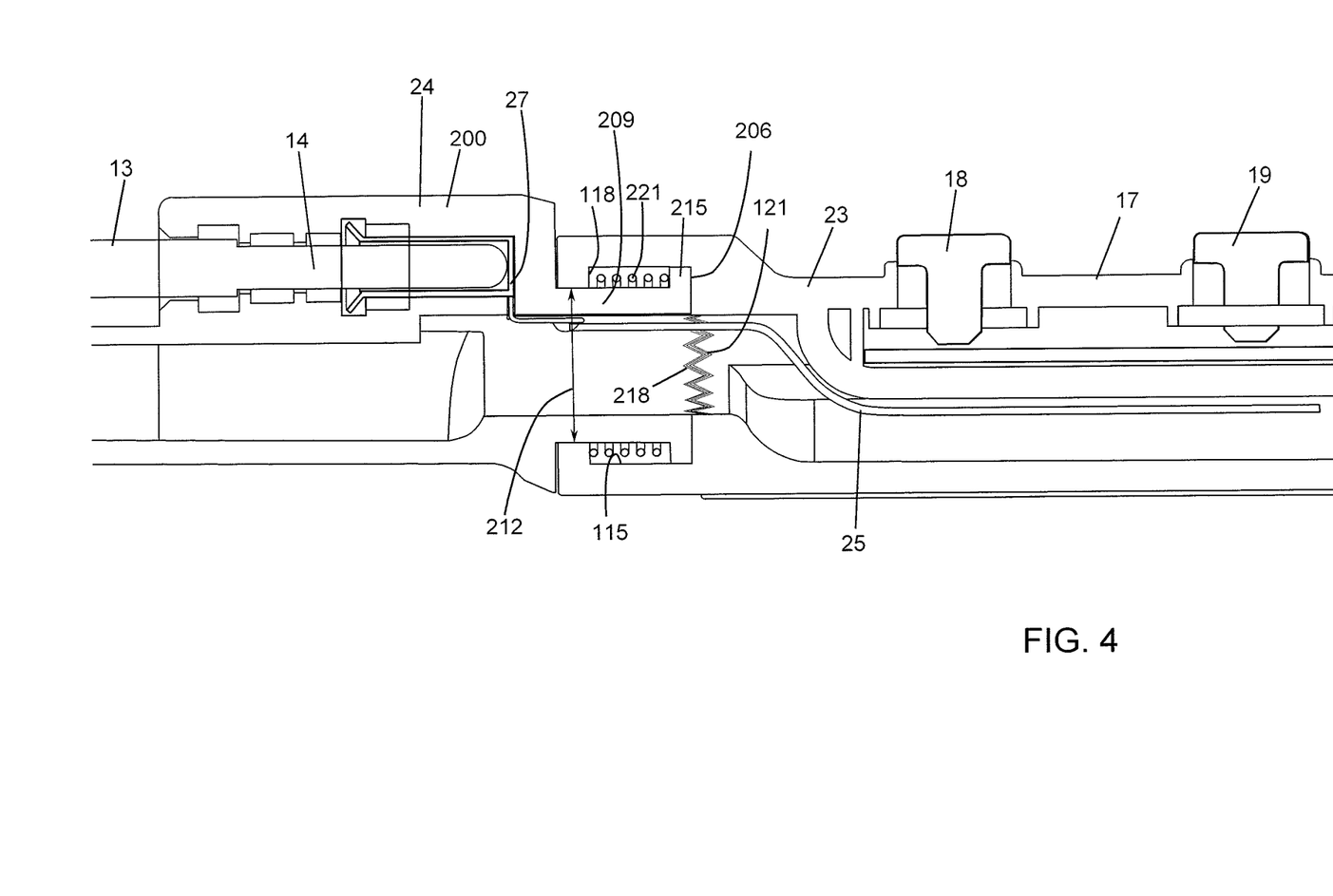
FIG. 4 is a partial sectional view taken along lines 4-4 of FIG. 1.

Electrode 11 has uninsulated portion 12, connected to insulated portion 13, which is connected to third portion 14 (FIGS. 3-4). As shown in FIG. 1, insulated portion 13 contains circular friction ridges 97. Electrode third portion 14 is reversibly and compressively engaged by hollow body 22. When engaged by hollow body 22, electrode 11 makes electrical connection with internal electrical contact 27, which is connected to electrical line 25 through buttons 18 and 19 within elongate body 22. When electrode 11 is engaged to body 22, portion 13 of electrode 11 is not encircled by body 22 and can be easily gripped by a user's fingers.

Electrical line 25 within elongated body 22 extends to the rear of body 22. At the rear of body 22, electrical line 25 may be disposed through the inside of a swivel joint 39 that connects between the body 22 and the vacuum exit port 30. Accordingly, electrical line 25 passes through the center of outlet port 30. By passing through outlet port 30, electric line 25 will not wrap around the external vacuum tube 16 when the device 10 is twisted relative to the external vacuum tube 16. This reduces the chance of discomfort for the user by minimizing rotational strains on the user's movement. Alternatively, the electrical wire 25 may exit body 22 adjacent to vacuum outlet port 30.

Vacuum tube 16 has an inlet facing generally towards the front end of body 22. Vacuum tube 16 is compressively engaged by the front end of the cavity in second member 24. Vacuum tube 16 is capable of telescopically extending from and retracting into the cavity. However, even when fully retracted, a portion of vacuum tube 16 will be protruding from body 22 and can be laterally gripped by a user. Electrode 11 may also telescopically extend from second member 24. The vacuum tube 16 and electrode 11 may extend together or separately.

Vacuum tube 16 is in fluid communication with hollow cavity 26, and vacuum exit port 30. Elongated body 22 contains bend 33 in its body near vacuum port 30 as shown in FIG. 1. The interface between bend 33 and body 22 is formed by the swivel joint 39.

Cut button 18 and coagulate button 19 may be disposed on top surface 17 of body 22.

Vacuum tube 16 may be constructed of a clear plastic material. The colors of buttons 18 and 19, body 22, and electrode insulated portion 13 may all be made distinct for ease of use. Electrical line 25 is flexible.

In FIG. 3, the first member 23 has an end 100 facing the second member 24. The end 100 has an opening 103 with a first diameter 106. The first member 23 has a chamber 109 defined therein. The chamber 109 has a second diameter 112 larger than the first diameter 106. The chamber 109 is bordered by a side wall 115 and a shoulder 118 extends between the side wall 115 and the opening 103. The chamber 109 is bordered by a bottom wall 128 with a first engagement surface 121 disposed thereon. The chamber 109 is disposed in fluid communication with the cavity 26.

Turning to FIG. 4, the second member 24 has a body 200 having a first end 203 (FIG. 3) and a second end 206. The body 200 has a first portion 209 having an outside diameter 212 sized to fit inside the opening 103 in the first member 100. The body 200 also has a flange 215 at the second end 206. The second member 24 has a second engaging surface 218 disposed near the second end 206 of the body 200. The second engaging surface 218 is configured to engage with the first engagement surface 121 to prevent rotation between the first member 23 and the second member 24 when the flange 215 is acted on by a biasing member 221. As shown the first and second engaging surfaces 121, 218 may comprise a plurality of interlocking teeth that intermesh when the surfaces are brought together via the biasing member 221. The biasing member 221 may comprise a coil spring disposed inside the chamber 109 between the shoulder 118 and the flange 215. As an alternative to the spring, the first member 23 and second member 24 may be reversibly coupled by means of a magnet. Other means for biasing the first member 23 and the second member 24 into locking engagement to prevent relative rotation will be apparent to those of ordinary skill in the art based on this disclosure.

The first and second engaging surfaces 121, 218 may be provided with numerous configurations providing any number of locking positions to provide adjustability of the position of the second member 24 relative to the first member 23. Regardless of the position of the second member 24 relative to the first member 23, the vacuum inlet 15 is maintained in fluid communication with the cavity 26 leading to the vacuum outlet 30 to provide suction to the inlet 15.

Operation

A user initially prepares first embodiment 10 by inserting electrode 11 into front end 28 of elongated body 22. By holding electrode 11 by insulated portion 13, the circular ridges along insulated portion 12 provide increased friction and grip for inserting electrode 11 into body 22. Electrode 11 is firmly pressed into body 22 such that electrode 11 makes electrical connection with internal electrical contact 27 within body 22. Since insulated portion 13 extends outside body 22 when electrode 11 is fully inserted, the user is able to insert the electrode without ever touching uninsulated portion 12 of electrode 11.

The user next adjusts vacuum tube 16 to the proper extension distance. Access to the lateral edges of vacuum tube 16 is not hindered by body 22 and the user can easily grip vacuum tube 16 by the lateral edges and telescopically adjust vacuum tube 16 to an appropriate extension amount.

Next, the position of the second member 24 relative to the first member 23 may be adjusted by gripping the second member 24 and pulling it away from the first member 23 against the force of the biasing member 221. Once the second member 24 is moved far enough in the axial direction away from the first member 23 to release the engagement of the interlocking teeth on the engaging surfaces 121, 218, the second member 24 can be rotated relative to the first member 23. Rotation of the second member 24 relative to the first member 23 provides adjustment of the electrode 11 and vacuum tube 16 relative to the remainder of the device 10. Once the second member 24 is released, the force of the biasing member 221 against the flange 215 causes the teeth of the engaging surfaces 121, 218 to interlock thereby fixing the position of the second member 24 relative to the first member 23. The flange 215 on the body 200 is wider than the opening 103 on the body 100 which prevents the second member 24 from being completely removed from the first member 23.

An external vacuum tube 37 is connected to outlet port 30, insuring that outlet port 24 is securely inserted such that an air-tight seal is formed. The opposing end of the external vacuum tube is connected to a vacuum source (not shown), and electrical line 25 is connected to an electrosurgical RF power source.

Figure 2:
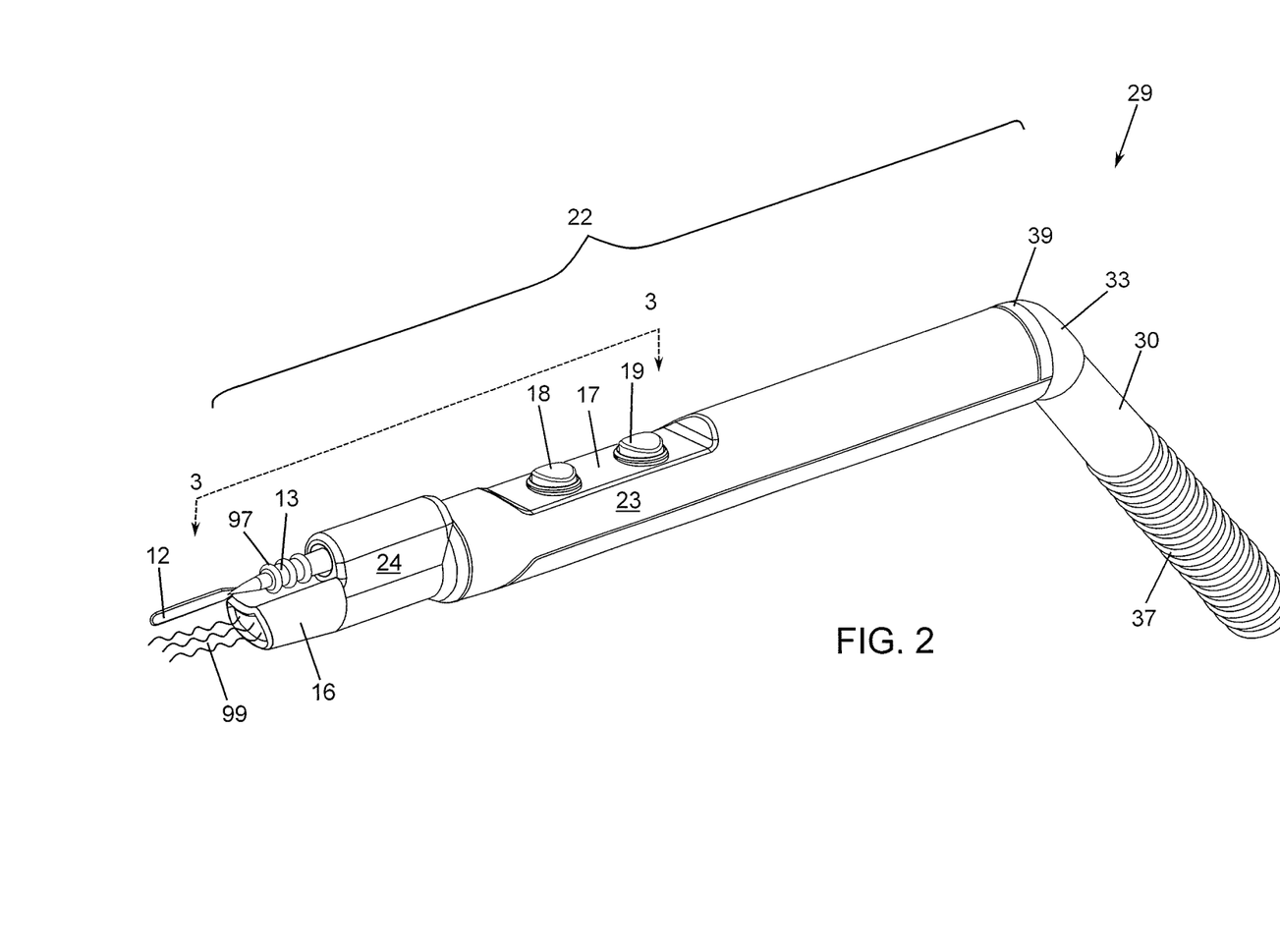
FIG. 2 is a perspective view of the first embodiment in a vacuum tube retracted configuration.

In preparation for electrosurgery, the user will grip body 22 similar to holding a pencil, and the user's thumb and non-index fingers will be placed on opposite sides of body 22. As best shown in FIG. 2, the shape of the device is ergonomically suited to a user's hand. When the user is ready to initiate electrosurgery, either button 18, for cutting, or button 19, for coagulating, will be depressed by the user's index finger. Pressing button 18 will cause current to pass from electrical line 25 to internal contact 27 and out electrode 11 to a patient's body with enough current to typically cause cutting of tissue. The electrical current through the tissue causes intense heat and smoke to form.

As shown in FIG. 2, the smoke 99 produced during electrosurgery is suctioned by vacuum tube 16. During surgery, the user may easily adjust the position of vacuum tube 16, either extending it closer to electrode portion 12 in order better capture smoke, or retracting it closer towards body 22 in order to provide the user with a less obstructed view of the surgical area.

The current flow and vacuum process is similar if the user uses coagulate button 19 instead of cut button 18. However, the current level for coagulate will be less than for cutting.

Vacuum tube 16 may be arranged above or below electrode portion 12 to capture smoke 99 from the treatment region due to convection. In the position above the electrode 12, vacuum tube 16 may be more likely to capture smoke than if it were arranged under electrode 13. Additionally, if vacuum tube 16 is not positioned on the bottom side of body 22, there may be a decreased risk of vacuum inlet 15 coming into contact with the patient's body which could cause trauma.

When, during the surgery, the user's hand is carrying the elongated body 22 along the body's longitudinal axis, the swivel joint 39 between the body 22 and outlet port 30 allows torsional strain to be released.

If during the surgery a different electrode style is needed, the user may easily remove electrode 11 from body 22. Since insulated portion 13 of electrode 11 is easily accessible to the user's fingers, the user may easily remove electrode 11 without touching electrically uninsulated areas of the electrode. This added safety feature helps to prevent the user from being burned from accidental activation of the electrosurgical device 10 during changing of the electrode 11.

Figure 5:
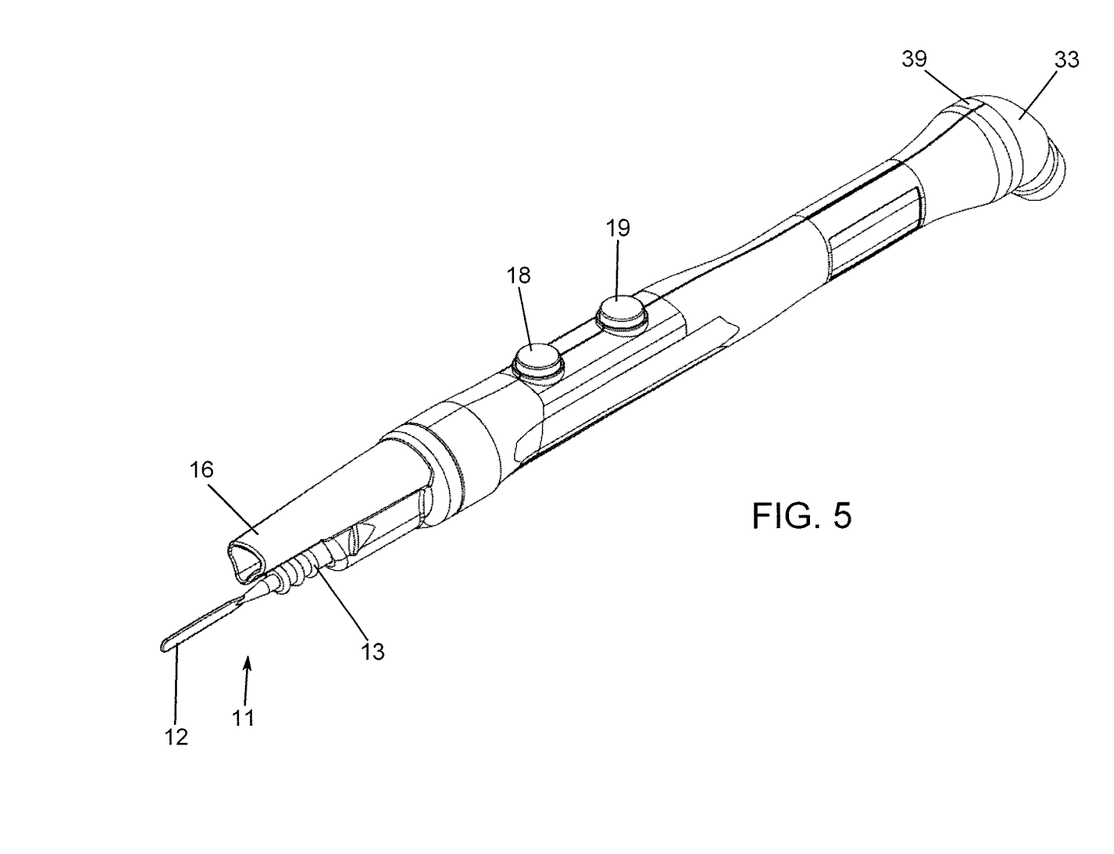
FIG. 5 is a perspective view of a second embodiment.
Figure 6:
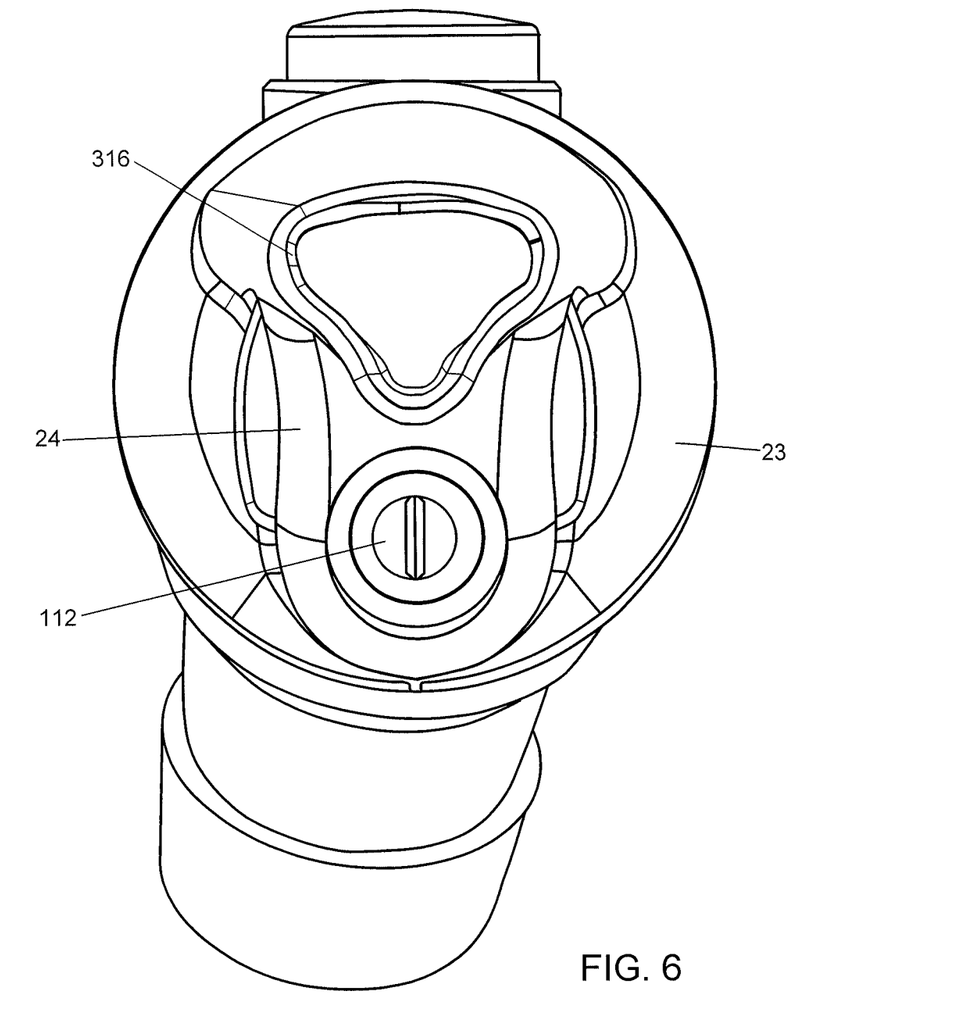
FIG. 6 is a front elevational view of the embodiment shown in FIG. 5.

The device of the present invention may contain an illumination light, light toggle button, and a light battery for providing greater illumination of the surgical region. The device may further contain a filter within cavity 26. The filter helps remove particulate matter, moisture, and odor from the smoke plume suctioned. The filter may contain an RFID tag which contains filter information as well as provides a tracking ID for the electrosurgical device. Also, vacuum control button allows the vacuum source to be switched on and off manually directly on the electrosurgical device. Alternately, an RF sensor, which is electrically isolated from the electrosurgical power source, may be connected to a remote vacuum source controller that is configured to automatically turn the vacuum source on when the sensor detects RF energy from either the cut or coagulate modes. As shown in FIGS. 5-6, an alternate embodiment includes vacuum tube 316. Vacuum tube 316 has a V-shape in cross-section near the electrode 11 such that the insulated portion 13 of the electrode 11 can be gripped without interference from the vacuum tube 316.

By designing the electrosurgical device such that an insulated portion of the electrode is available to be grabbed when the electrode is fully inserted, the insertion and removal of electrodes is made easier and safer. The user is less likely to get accidentally burned when changing the electrode since he/she can grid the electrode on an electrically insulated portion. Further, the use of friction ridges on the insulated portion of the electrode and the elongated body sides, the chance that the device slips in the user's hands is reduced. This is particularly important since the surgical process is likely to cause blood and other slippery body fluids to end up on the device.

Figures 7, 8:
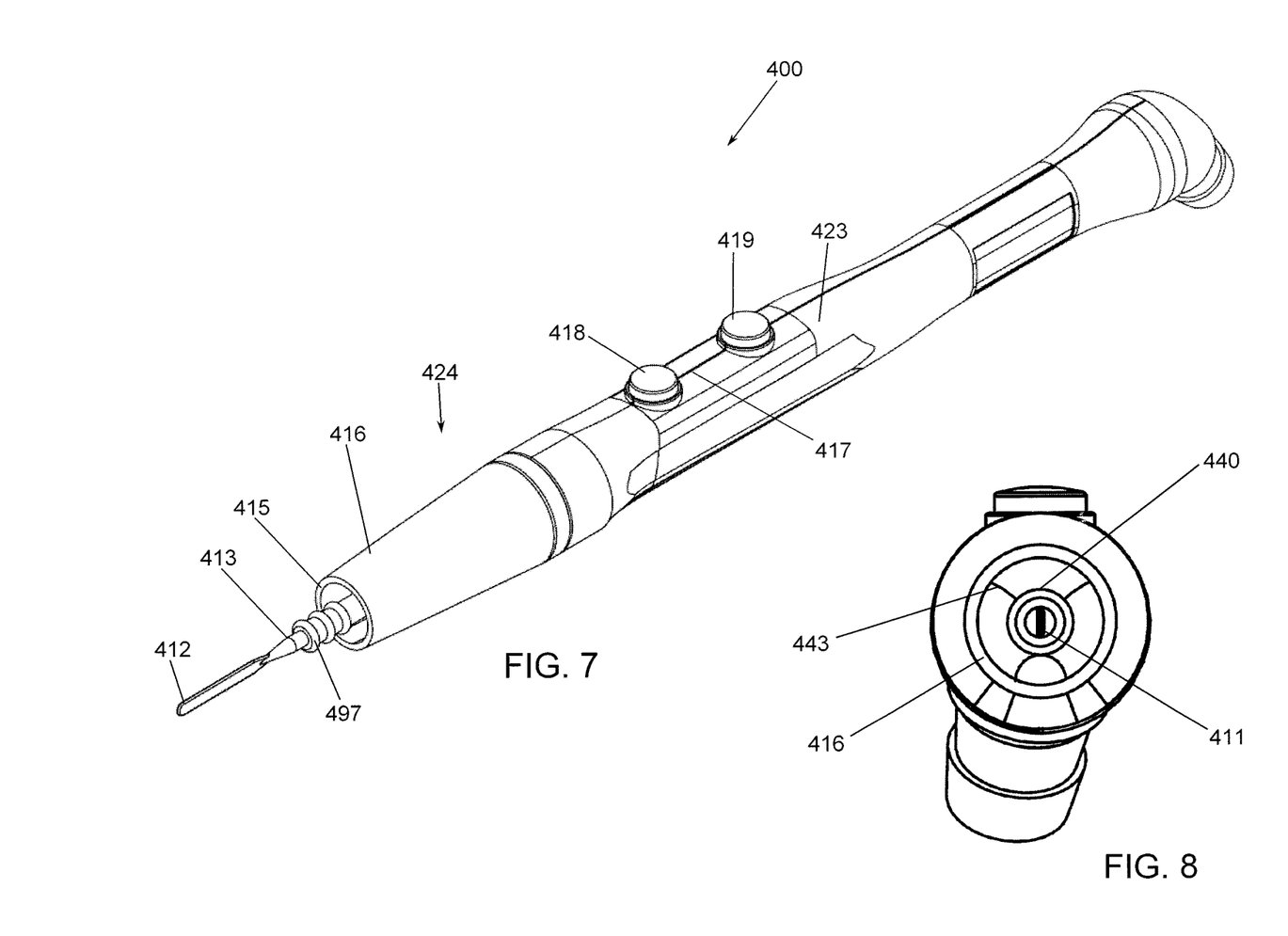
FIG. 7 is a perspective view of an alternate embodiment.
FIG. 8 is a front elevational view of the embodiment shown in FIG. 7.

In FIG. 7, an alternate embodiment includes a hollow body 400 formed by a first member 423 and a second member 424. The second member 424 is capable of rotated relative to the first member 423. The second member 424 has a vacuum tube 416 that surrounds a portion of the electrode 411. As shown, the un-insulated portion 412 and the insulated portion 413 with circular ridges 497 extend beyond the vacuum inlet 415. A cut button 418 and a coagulate button 419 are disposed on the exterior surface 417. The first member 423 and the second member 424 are held together in a locked position by means of a biasing member or the like as described above in connection with FIGS. 1-4. The user may adjust the position of the second member 424 by pulling it forward, rotating it into a new position, and then releasing it.

Turning to FIG. 8, the electrode 411 is received in a socket 440 that is supported inside the vacuum tube 416. As shown, the electrode 411 is disposed in the center of the vacuum tube 416. Other configurations with the electrode 411 inside the vacuum tube 416 but offset from the center may also be suitable for some applications. The socket 440 is supported from the inside of the tube 416 or from other support structure disposed inside the body 400. An electrical contact (not shown) disposed at the end of the socket 440 is electrically connected to a wire 425 for supplying power to the electrode 411.

The disclosed embodiments also increase surgical efficiency through the illumination offered by an attached light, the reduction of rotational strain by the external vacuum tube swivel and electrical line positioning within the swivel, and the button for controlling the vacuum source. Additionally, the RF sensor within the electrosurgical device allows the vacuum source to be automatically controlled by a circuit which is electrically isolated from the electrosurgical power supply.

Having fully disclosed the preferred form of the electrosurgical device and several variations thereof, persons skilled in the art will readily appreciate that various additional changes may be made without departing from the scope of the invention as set forth in the following claims.

The invention claimed is:

1. An electrosurgical device comprising:
   an electrode having a first portion with an exterior that is electrically uninsulated, a second portion with an exterior that is electrically insulated, and a third portion;
   an elongated hollow body formed by a first member and a second member and having an internal cavity, the second member capable of rotating relative to the first member, the elongated hollow body having a front end, a rear end, an external surface, and an electrical wire arranged within the elongated hollow body,
      wherein the second member is configured to reversibly receive the third portion of the electrode at the front end of the elongated hollow body such that electrical contact is made between the electrode and the electrical wire and the second portion of the electrode is not surrounded by the elongated hollow body;
   a first button for controlling a current flow at a first level to the electrode and arranged on the external surface of the first member of the elongated hollow body;
   a vacuum tube engaged by the second member of the elongated hollow body, wherein the vacuum tube is arranged adjacent to the electrode, the vacuum tube having a vacuum inlet; and
   a vacuum outlet port arranged near the rear end and the first member, and
   wherein the vacuum outlet port, internal cavity, and vacuum inlet are disposed in fluid communication with each other,
   wherein the first member has an end with an opening facing the second member, the opening including a first engagement surface, the second member has a first end and a second end, the second member having a first portion having an outside diameter sized to fit inside the opening in the first member and a flange at the second end, the second member having a second engaging surface disposed near the second end, the second engaging surface configured to engage with the first engagement surface to prevent rotation of the second member relative to the first member and the vacuum outlet port when the flange is acted on by a biasing member,
   wherein the second member is operable to rotate relative to the first member and the vacuum outlet port when the biasing member is compressed by the flange, and
   wherein the vacuum outlet port, the internal cavity, and the vacuum inlet maintain fluid communication between one another regardless of a rotational position of the first member with respect to the second member.

2. An electrosurgical device as set forth in claim 1 wherein the elongated hollow body is ergonomically shaped to be received by a user's hand.

3. An electrosurgical device as set forth in claim 1, wherein the biasing member comprises a coil spring disposed between the flange on the second member and the shoulder on the first member.

4. An electrosurgical device as set forth in claim 1 wherein the electrode is monopolar, bipolar, or sesquipolar.

5. An electrosurgical device as set forth in claim 1 and further comprising a second button for controlling a current flow at a second level to the electrode.

6. An electrosurgical device as set forth in claim 5 and further comprising a third button for controlling a vacuum source.

7. An electrosurgical device as set forth in claim 1 and further comprising:
   a light source arranged to illuminate an area near the electrode;
   a battery for providing power to the light source; and,
   a button for controlling the light.

8. An electrosurgical device as set forth in claim 1 and further a swivel joint between the elongated hollow body and the outlet port; and wherein the electrical wire passes through the swivel joint.

9. An electrosurgical device as set forth in claim 1 further comprising a filter having an RFID tag containing filter information.

10. An electrosurgical device as set forth in claim 1 wherein the vacuum inlet has a substantially rectangular cross section.

11. An electrosurgical device comprising:
    an electrode having a first portion with an exterior that is electrically uninsulated, a second portion with an exterior that is electrically insulated, and a third portion;
    an elongated hollow body formed by a first member and a second member and having an internal cavity, the second member capable of rotating relative to the first member, wherein the first member has an end facing the second member, the end having an opening with a first diameter, the first member having a chamber defined therein, the chamber having a second diameter larger than the first diameter, the chamber bordered by a side wall and a shoulder extending from the side wall and the opening, the chamber bordered by a bottom wall with a first engagement surface disposed thereon, the chamber disposed in fluid communication with the cavity, wherein the second member has a first end and a second end, the second member having a first portion having an outside diameter sized to fit inside the opening in the first member and a flange at the second end, the second member having a second engaging surface disposed near the second end, the second engaging surface configured to engage with the first engagement surface to prevent rotation between the first member and the second member when the flange is acted on by a biasing member, wherein the second member is operable to rotate relative to the first member when the biasing member is compressed by the flange, the elongated hollow body having a front end, a rear end, an external surface, and an electrical wire arranged within the elongated hollow body, the second member configured to reversibly receive the third portion of the electrode at the front end of the elongated hollow body such that electrical contact is made between the electrode and the electrical wire and the second portion of the electrode is not surrounded by the elongated hollow body;

a first button for controlling a current flow at a first level to the electrode and arranged on the external surface of the first member of the elongated hollow body;

a vacuum tube engaged by the elongated hollow body on the second member and arranged adjacent the electrode, the vacuum tube having a vacuum inlet; and a vacuum outlet port arranged near the rear end, and wherein the outlet port, internal cavity, and vacuum inlet are disposed in fluid communication with each other, and wherein the outlet port, the internal cavity, and the vacuum inlet maintain fluid communication between one another regardless of a rotational position of the first member with respect to the second member.

12. An electrosurgical device as set forth in claim 11 wherein the elongated hollow body is pencil shaped.

13. An electrosurgical device as set forth in claim 11 wherein the electrode is monopolar, bipolar, or sesquipolar.

14. An electrosurgical device as set forth in claim 11 and further comprising a second button for controlling a current flow at a second level to the electrode.

15. An electrosurgical device as set forth in claim 14 and further comprising a third button for controlling a vacuum source.

16. An electrosurgical device as set forth in claim 11 wherein the vacuum inlet has a substantially rectangular cross section.

* * * * *